(12) United States Patent
Samadi

(10) Patent No.: US 10,775,272 B2
(45) Date of Patent: Sep. 15, 2020

(54) RUBBER FOOTPRINT AND ROLLING RESISTANCE MEASUREMENT

(71) Applicant: Ali Samadi, Urmia (IR)

(72) Inventor: Ali Samadi, Urmia (IR)

(*) Notice: Subject to any disclaimer, the term of this patent is extended or adjusted under 35 U.S.C. 154(b) by 93 days.

(21) Appl. No.: 16/209,977

(22) Filed: Dec. 5, 2018

(65) Prior Publication Data

US 2019/0107464 A1    Apr. 11, 2019

Related U.S. Application Data

(60) Provisional application No. 62/594,558, filed on Dec. 5, 2017.

(51) Int. Cl.
| | | |
|---|---|---|
| *G01M 17/02* | (2006.01) | |
| *G01N 33/44* | (2006.01) | |
| *G01N 19/02* | (2006.01) | |

(52) U.S. Cl.
CPC .......... *G01M 17/022* (2013.01); *G01N 19/02* (2013.01); *G01N 33/445* (2013.01)

(58) Field of Classification Search
USPC ................................................ 73/146–146.8
See application file for complete search history.

(56) References Cited

U.S. PATENT DOCUMENTS 4,373,566 A * 2/1983 Hirakawa ............... B60C 11/01
152/523
4,489,598 A * 12/1984 Beebe ................ G01M 17/022
73/146
4,584,873 A * 4/1986 Ongaro ............... G01M 17/022
73/146

(Continued)

FOREIGN PATENT DOCUMENTS

| WO | WO-2010101159 A1 * | 9/2010 | .......... G01M 17/022 |
| WO | WO-2017207180 A1 * | 12/2017 | .......... G01M 17/022 |
| WO | WO-2018056081 A1 * | 3/2018 | ............ B60C 19/00 |

*Primary Examiner* — Andre J Allen
(74) *Attorney, Agent, or Firm* — Bajwa IP Law Firm; Haris Zaheer Bajwa

(57) ABSTRACT

A system for measuring rolling resistance of a substrate may include a transparent support member including a contact surface, a rolling member including a cylindrical convex surface with the substrate attached on the cylindrical convex surface, the cylindrical convex surface placed on the contact surface, an oscillation mechanism coupled with the rolling member configured to drive an oscillatory rotational movement of the rolling member about a longitudinal axis of the rolling member. The oscillation mechanism may include two parallel arms attached at their respective midpoints to either base ends of the rolling member on a pivot axis overlapping the longitudinal axis of the rolling member, the two parallel arms attached to one another at respective ends of the two parallel arms by two links, and two adjustable weights, each of the two adjustable weights mounted on a respective link of the two links. The exemplary system may further include a light source arranged at one side of the transparent body such that light emitted from the light source reflected within the transparent support member, and an image capturing device placed below the contact surface configured to capture images of contact patch of the substrate through the transparent support member.

20 Claims, 10 Drawing Sheets

(56) References Cited

U.S. PATENT DOCUMENTS

| | | | | |
|---|---|---|---|---|
| 5,635,623 | A * | 6/1997 | Simon | G01M 17/02 |
| | | | | 73/9 |
| 6,494,076 | B1 * | 12/2002 | Gent | G01N 19/02 |
| | | | | 73/9 |
| 2019/0178753 | A1 * | 6/2019 | Chang | G01M 17/022 |
| 2020/0049593 | A1 * | 2/2020 | Eisenbeiss | G01M 17/022 |

* cited by examiner

RUBBER FOOTPRINT AND ROLLING RESISTANCE MEASUREMENT

CROSS-REFERENCE TO RELATED APPLICATION

This application claims the benefit of priority from U.S. Provisional Patent Application Ser. No. 62/594,558, filed on Dec. 5, 2017, and entitled "SIMULTANEOUS MEASUREMENT OF RUBBER FOOTPRINT AND ROLLING RESISTANCE," which is incorporated herein by reference in its entirety.

TECHNICAL FIELD

The present disclosure relates to systems and methods for testing and measuring properties of materials, particularly relates to systems and methods for measurement of rubber footprint and rolling resistance of rubber substrates.

BACKGROUND

Rolling resistance of a tire may be defined as the amount of energy dissipated in rolling of the tire per unit normal load and unit distance travelled by the tire. For a tire made of rubber, the main contributor to rolling resistance is hysteresis due to the viscoelastic behavior of rubber. Repeated cycles of deformation and recovery experienced by a rubber tire as it rotates under the weight of a vehicle leads to hysteresis energy loss being dissipated from the rubber tire as heat. The rolling resistance may cause an increase in fuel consumption and vehicle greenhouse gas emissions. Therefore, there is a need for designing rubber tires with lower rolling resistance. To this end, systems and methods are required for measuring and comparing rolling resistances and energy dissipations in rubber tires under rolling conditions.

Developing systems and methods for measuring the rolling resistance of a rubber tire may have numerous challenges such as finding optimal ways of applying the rolling driving force, measuring the rolling resistance, and providing a continuous flat surface for rolling. Systems and methods have been developed in which rubber tires are rolled against a rotating drum using complex mechanical and electronic devices to apply the rolling driving force and measuring the rolling resistance. However, in such systems and methods due to the complexity of the system, losses in gears and motors may not be properly accounted for, which may considerably affect the accuracy of the measurements.

In order to replace the complex mechanical and electronic devices in the aforementioned measuring systems, an independent pendulum driving force may be utilized to create a reciprocating rolling movement that may simulate a continuous rolling motion of the rubber tire. Damping of the oscillatory motion of the rubber tire that is connected to the pendulum may be utilized for measuring the rolling resistance of the rubber tire. However, systems and methods that are developed based on damping of oscillatory motion of a pendulum need to be further improved to ensure a repeatable release of the pendulum at a specific angle, a straight rolling path for the rubber tire, and a balanced pendulum motion against centrifugal forces acting on the pendulum. There is further a need for developing systems and methods that allow for an accurate non-contact measurement of rolling resistance without imposing unwanted limitations in the oscillatory rolling motion of the rubber tire.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

According to one or more exemplary embodiments, the present disclosure is directed to a system for measuring rolling resistance of a substrate. The exemplary system may include a transparent support member including a transparent contact surface, a rolling member including a cylindrical convex surface with the substrate attached on the cylindrical convex surface, the cylindrical convex surface configured to be in constant contact with the contact surface, an oscillation mechanism coupled with the rolling member configured to drive an oscillatory rotational movement of the rolling member about a longitudinal axis of the rolling member. The oscillation mechanism may include two parallel arms attached at their respective midpoints to either base end of the rolling member on a pivot axis overlapping the longitudinal axis of the rolling member, the two parallel arms attached to one another at respective ends of the two parallel arms by two links, and two adjustable weights, each of the two adjustable weights mounted on a respective link of the two links. The exemplary system may further include a light source arranged at one side of the transparent body such that light from the light source may be emitted within the transparent support member, and an image capturing device placed below the contact surface that may be configured to capture images of contact patch of the substrate through the transparent support member.

In an exemplary embodiment, the exemplary system may further include a control unit that may be coupled with the image capturing device. The control unit may include a processor, and a memory that may be configured to store executable instructions to cause the processor to identify a pressure center for the rubber footprint of the substrate based on the images captured by the image capturing device, where the pressure center may correspond to a region within the images of the rubber footprint with the highest black pixel density, and to obtain a rate of change in a motion range of the rubber footprint by tracking back and forth motion of the pressure center of the images.

In an exemplary embodiment, the memory may be configured to store further executable instructions to cause the processor to calculate a pressure distribution within the rubber footprint by dividing an average black pixel density of the captured images by the highest black pixel density in the captured images.

In an exemplary embodiment, the memory may be configured to store further executable instructions to cause the processor to calculate rolling resistance of the substrate by equation below:

$$RR = \sum_{n=0}^{n=\infty} \frac{2mgL[\cos\theta_0]}{R\theta_n} = \frac{2mgL[\cos\theta_0]}{\sum_{n=0}^{n=\infty} R\theta_n}$$

where, RR is the amount of rolling resistance, m is the mass of each of the two adjustable weights, g is the standard gravity, L is the distance between either one of the two adjustable weights from a center of rolling member, $\theta_0$ is the initial angle of oscillation mechanism with a normal axis of the transparent support member, $\theta_n$ is the angle of oscillation mechanism with the normal axis of the transparent support member in an $n^{th}$ oscillation of the rocking motion of the rolling member, and R is a radius of the rolling member.

In an exemplary embodiment, the longitudinal axis of the rolling member may be an axis passing through a center of the mass of the rolling member on a similar plane with a rolling direction of the rolling member perpendicular to the rolling direction.

In an exemplary embodiment, the rolling member may further include two adjustable side-weights that may be removably attached to either base ends of the rolling member.

In an exemplary embodiment, the exemplary system may further include a main chassis. The main chassis may include a base support, and a mounting rig that may be attached on the base support. The mounting rig may include two parallel vertical poles mounted on the base support, and a horizontal pole mounted between the two parallel vertical poles with an adjustable height relative to the transparent support member.

In an exemplary embodiment, the exemplary system may further a weight release mechanism that may be mounted on the horizontal pole. The weight release mechanism may include a shaft that may be pivotally mounted on the horizontal pole at a first end of the shaft, and a receptacle that may be attached to a second end of the shaft. In an exemplary embodiment, the receptacle may include an electromagnet selectively engaging one of the two adjustable weights.

In an exemplary embodiment, the receptacle may be a longitudinal section of a cylinder including a semi-cylindrical recess longitudinally formed on the receptacle, where one of the two adjustable weights may be received within the semi-cylindrical recess.

In an exemplary embodiment, the image capturing device may be mounted on the base support below the transparent support member. The image capturing device may be enclosed by a cover. The cover may extend downward from immediately below a lower surface of the transparent support member to immediately above an upper surface of the base support.

In an exemplary embodiment, the rolling member may be a cylinder-shaped roller with two adjustable side weights removably attached to either base ends of the cylinder-shaped roller.

In an exemplary embodiment, the rolling member may be a longitudinal section of a cylinder including a lower cylindrical convex surface and an upper flat surface, the substrate attached under the lower cylindrical convex surface.

In an exemplary embodiment, the rolling member may further comprises adjustable weights removably mounted on the upper flat surface. In an exemplary embodiment, the rolling member may be a wheel with the substrate attached to a rim of the wheel.

In an exemplary embodiment, the transparent support member may be a box-shaped member with parallel and flat upper surface and lower surface. The upper surface may provide the transparent contact surface.

According to one or more exemplary embodiments, the present disclosure is directed to a method for testing properties of a rubber substrate. The method may include attaching the rubber substrate on a convex cylindrical surface of a rolling member, rocking the rolling member with an initial amplitude over a transparent surface, capturing consecutive images of a rubber footprint of the rubber substrate from under the transparent surface, obtaining, using one or more processors, a rate of change in the initial amplitude of the rocking motion of the rolling member on the transparent surface based at least in part on a rate of change in a range of back and forth motion of the rubber footprint by optically processing the captured consecutive images, and calculating, using one or more processors, an amount of rolling resistance for the rubber substrate based at least in part on the rate of change in the amplitude of the rocking motion of the rolling member on the transparent surface.

In an exemplary embodiment, rocking the rolling member with the initial amplitude over the transparent surface may include coupling the rolling member with an oscillation mechanism. The oscillation mechanism may include two parallel arms attached at their respective midpoints to either base ends of the rolling member on a pivot axis overlapping a longitudinal axis of the rolling member, the two parallel arms attached to one another at respective ends of the two parallel arms by two links, and two adjustable weights, each of the two adjustable weights mounted on a respective link of the two links. In an exemplary embodiment, rocking the rolling member with the initial amplitude over the transparent surface may further include adjusting the initial amplitude by adjusting an initial orientation of the two parallel arms with respect to the transparent surface, and releasing the oscillation mechanism from the initial orientation to freely oscillate in a rocking motion back and forth about the longitudinal axis of the rolling member.

In an exemplary embodiment, obtaining the rate of change in the initial amplitude of the rocking motion of the rolling member on the transparent surface may include optically processing the captured images to track the position of the rubber footprint on transparent surface at every instant of the test.

In an exemplary embodiment, obtaining the rate of change in the initial amplitude of the rocking motion of the rolling member on the transparent surface may include processing the captured images to find a pressure center for the rubber footprint by finding a region with the highest black pixel density, and calculating, at any given moment a distance between the pressure center and a reference line.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1A:
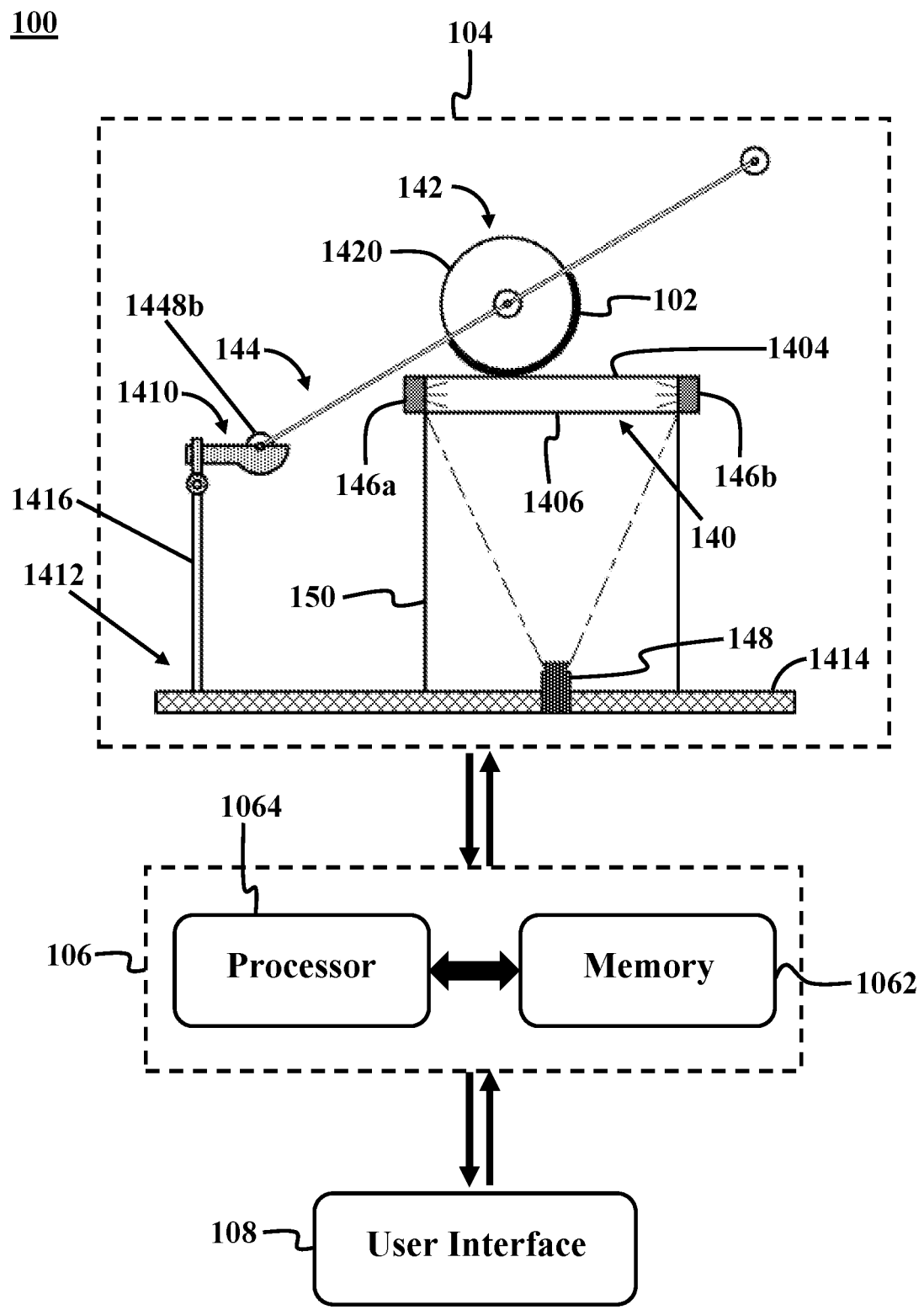
FIG. 1A illustrates a block diagram of a system for measuring rolling resistance of a substrate, consistent with one or more exemplary embodiments of the present disclosure.

In the following detailed description, numerous specific details are set forth by way of examples to provide a thorough understanding of the relevant teachings related to the exemplary embodiments. However, it should be apparent that the present teachings may be practiced without such details. In other instances, well known methods, procedures, components, and/or circuitry have been described at a relatively high level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be plain to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Contact patch or rubber footprint is the portion of a rubber tire that is in contact with a road surface. In the assessment of a tire, especially a pressurized rubber tire, factors like the pressure distribution within the contact patch of the tire, as well as the size and shape of the contact patch are factors that may affect the wear characteristics of the rubber tire. Furthermore, the amount of energy dissipation during the rolling motion of the rubber tire due to the rolling resistance is another important design factor in manufacturing rubber tires. Designing an efficient rubber tire may depend on accurate measurement and evaluation of the rubber footprint and rolling resistance of a rubber substrate that is used for manufacturing that rubber tire.

The present disclosure is directed to exemplary systems and exemplary methods for testing properties of a rubber substrate. An exemplary system for testing properties of a rubber substrate may be utilized to simulate rolling motion of the rubber substrate on a surface and then to measure and calculate the shape and size of the rubber footprint of the rubber substrate on the surface, the pressure distribution within the rubber footprint of the substrate, and the amount of the rolling resistance of the substrate. An exemplary system for testing properties of a rubber substrate may include a rolling member with a convex cylindrical surface, on which a rubber substrate may be attached. The rolling member of different exemplary embodiments of the present disclosure may be placed over a transparent surface and may further be coupled with an oscillation mechanism. The exemplary oscillation mechanism may cause a rocking motion of the exemplary rolling member back and forth on the transparent surface. The mechanism may also cause pressing of the substrate onto the transparent surface while an image-capturing device may capture images of the rubber footprint of the substrate from under the transparent surface. The exemplary system may further include a control unit that may receive the captured images and may process the images to measure and calculate the shape and size of the rubber footprint of the rubber substrate on the surface, the pressure distribution within the rubber footprint of the substrate, and the amount of the rolling resistance of the substrate.

FIG. 1A illustrates a block diagram of a system 100 for testing properties of a substrate 102, consistent with one or more exemplary embodiments of the present disclosure. In an exemplary embodiment, system 100 may include a testing apparatus 104 that may be utilized for simulating a rolling movement of substrate 102 on a surface and capturing consecutive images of the rolling movement of substrate 102 on the surface, a control unit 106 coupled with testing apparatus 104 and configured to receive and process the captured consecutive images, and optionally a user interface unit 108.

Figure 1B:
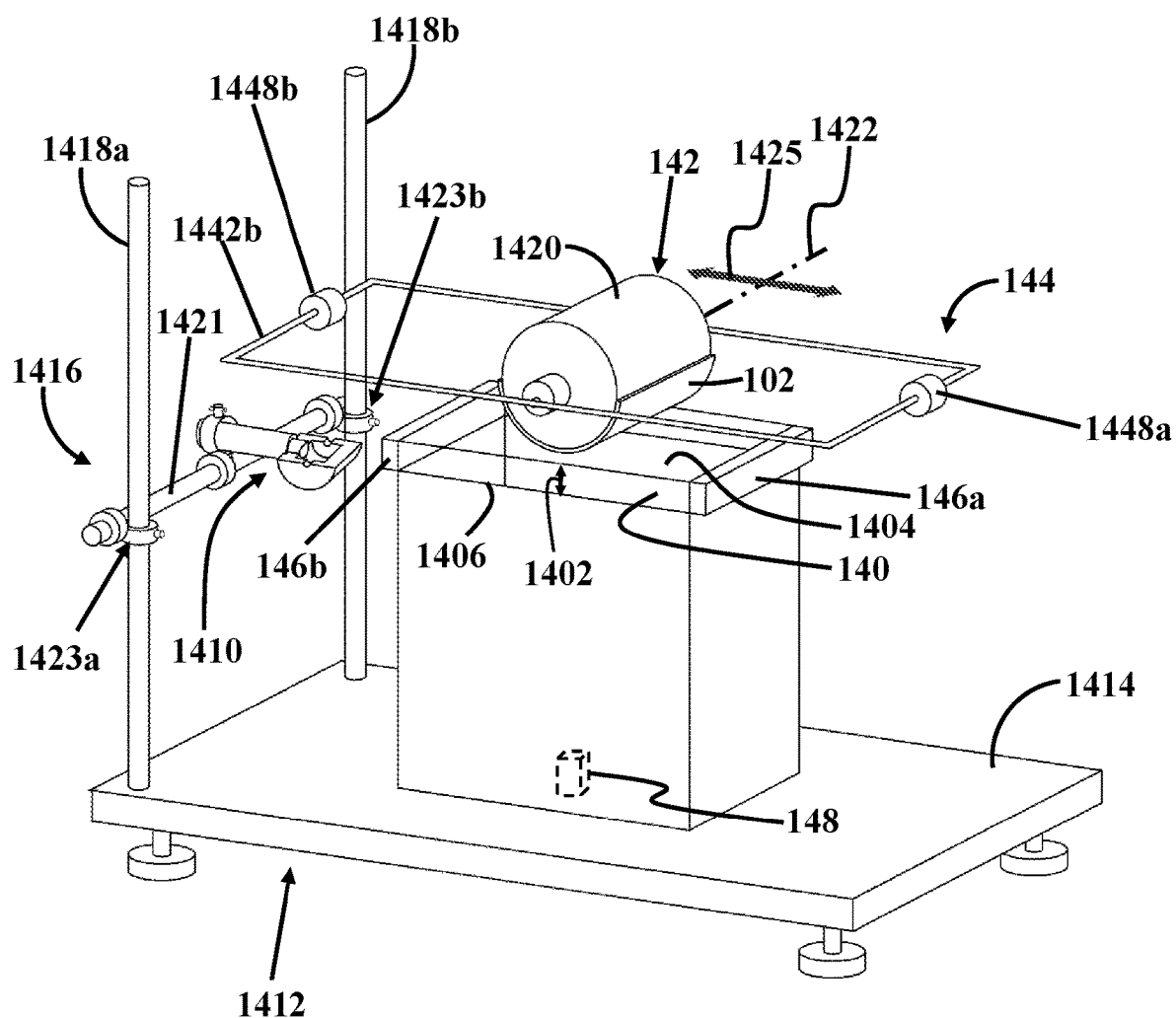
FIG. 1B illustrates a perspective view of measurement apparatus, consistent with one or more exemplary embodiments of the present disclosure.

FIG. 1B illustrates a perspective view of testing apparatus 104, consistent with one or more exemplary embodiments of the present disclosure. Referring to FIGS. 1A and 1B, in an exemplary embodiment, testing apparatus 104 may include a transparent support member 140, a rolling member 142 that may include a cylindrical convex surface 1420 on which substrate 102 may be attached, an oscillation mechanism 144 that may be coupled with rolling member 142 and may be configured to drive an oscillatory rocking motion of rolling member 142 about a longitudinal axis 1422 of rolling member 142 along a rolling direction as shown by arrow 1425, light sources 146a-b, and an image capturing device 148 that may be placed below transparent support member 140 and may be configured to capture consecutive images of rubber footprint of substrate 102 through transparent support member 140.

In an exemplary embodiment, transparent support member 140 may be a box-shaped member that may be made of a transparent material such as glass with a predetermined thickness 1402. An upper surface 1404 and a lower surface 1406 of transparent support member 140 may be smooth and flat and may be parallel to each other. Upper surface 1404 of transparent support member 140 may provide a transparent surface on which substrate 102 may rock back and forth.

In an exemplary embodiment, light sources 146a-b may be attached on either side of transparent support member 140 and may be arranged such that the light from light sources 146a-b is emitted within the thickness of transparent support member 140. In an exemplary embodiment, such configuration of light sources 146a-b may provide enough light for image capturing device 148 to efficiently capture the reflected light from the rubber footprint of substrate 102 through transparent support member 140. In an exemplary embodiment, light sources 146a-b may include long light emitting devices such as fluorescent lamps with a predetermined length or a number of light sources that may be place at regular intervals along the sides of transparent support member 140 in order to supply a stable light within transparent support member 140.

Figure 2A:
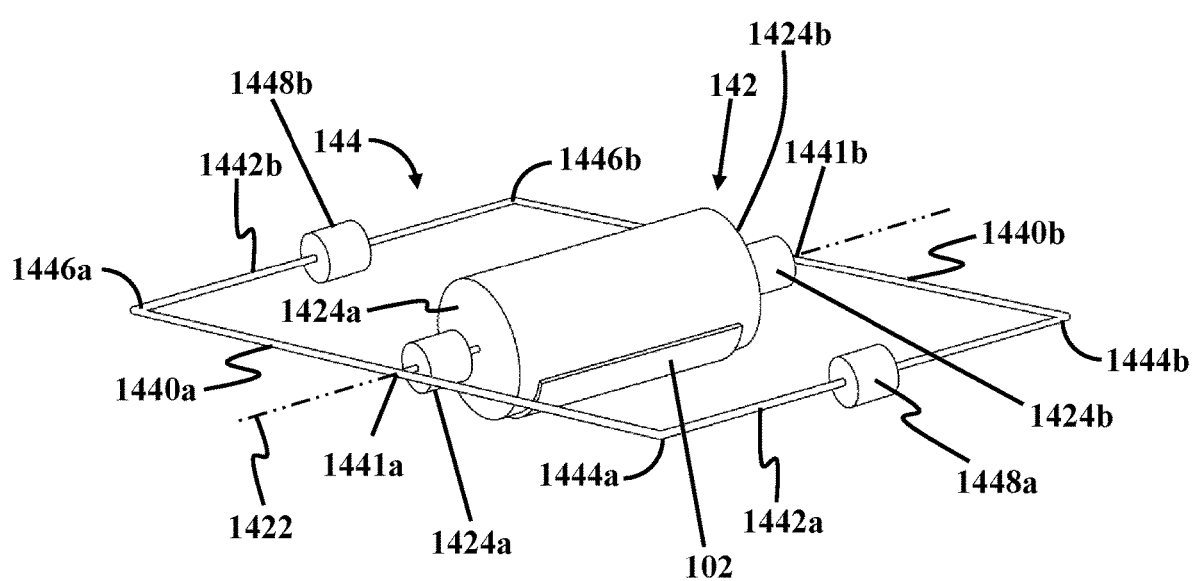
FIG. 2A illustrates a perspective view of an oscillation mechanism coupled with a rolling member, consistent with one or more exemplary embodiments of the present disclosure.

FIG. 2A illustrates a perspective view of oscillation mechanism 144 coupled with rolling member 142, consistent with one or more exemplary embodiments of the present disclosure. In an exemplary embodiment, oscillation mechanism 144 may include two parallel arms 1440a-b that may be attached at their respective midpoints 1441a-b to either base ends 1424a-b of rolling member 142 on a pivot axis overlapping longitudinal axis 1422 of rolling member 142. In an exemplary embodiment, two parallel arms 1440a-b may further be attached together at respective ends of two parallel arms 1440a-b by two links 1442a-b. For example, first ends 1444a-b of two parallel arms 1440a-b may be connected by link 1442a and second ends 1446a-b of two parallel arms 1440a-b may be connected by link 1442b.

In an exemplary embodiment, oscillation mechanism 144 may further include two adjustable weights 1448a-b. Each of two adjustable weights 1448a-b may be mounted on a respective link of the two links 1442a-b. For example, adjustable weight 1448a may be mounted on link 1442a and adjustable weight 1448b may be mounted on link 1442b. In an exemplary embodiment, links 1442a-b may either be attached or integrally formed with parallel arms 1440a-b.

In an exemplary embodiment, rolling member 142 may be a cylinder-shaped roller capable of assuming an oscillatory rocking motion back and forth about longitudinal axis 1422, when urged by oscillation mechanism 144, which will be described later in this disclosure. In exemplary embodiments, such configuration of the rolling member 142 and oscillation mechanism 144 may allow for simulating a rolling movement of substrate on a surface under a predetermined load without a need for a long and impractical test surface on which rolling member 142 may assume a full rolling motion about longitudinal axis 1422. In an exemplary embodiment, in order to adjust the predetermined load on substrate 102, rolling member 142 may further include two adjustable side-weights 1426a-b that may be removably attached to either base ends 1424a-b of rolling member 142. In exemplary embodiments, in order to increase the load exerted on substrate 102, adjustable weights 1426a-b may be replaced by heavier weights and in order to reduce the load exerted on substrate 102, adjustable weights 1426a-b may be replaced by lighter weights or be removed all together.

Figure 2B:
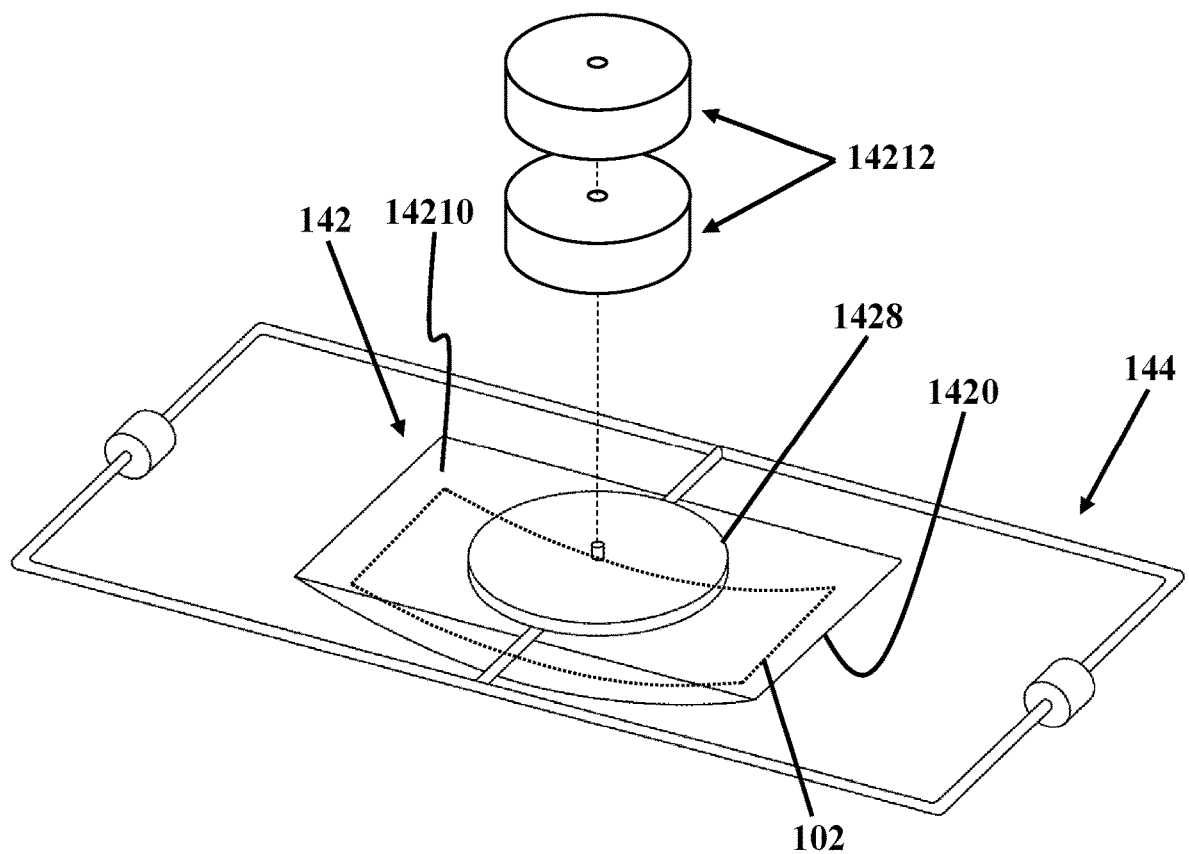
FIG. 2B illustrates a perspective view of an oscillation mechanism coupled with a rolling member, consistent with one or more exemplary embodiments of the present disclosure.

FIG. 2B illustrates a perspective view of oscillation mechanism 144 coupled with rolling member 142, consistent with one or more exemplary embodiments of the present disclosure. In an exemplary embodiment, rolling member 142 may be a longitudinal section of a cylinder with substrate 102 attached under cylindrical convex surface 1420 of rolling member 142. In an exemplary embodiment, in order to adjust the predetermined load on substrate 102, rolling member 142 may further include a weight support structure 1428 mounted or attached on a flat upper surface 14210 of rolling member 142. Weight support structure 1428 may be sized and shaped to be capable of receiving weights 14212. In an exemplary embodiment, in order to increase the load exerted on substrate 102, weights 14212 may be added onto weight support structure 1428 and in order to reduce the load exerted on substrate 102, weights 14212 may be removed from weight support structure 1428.

Figure 2C:
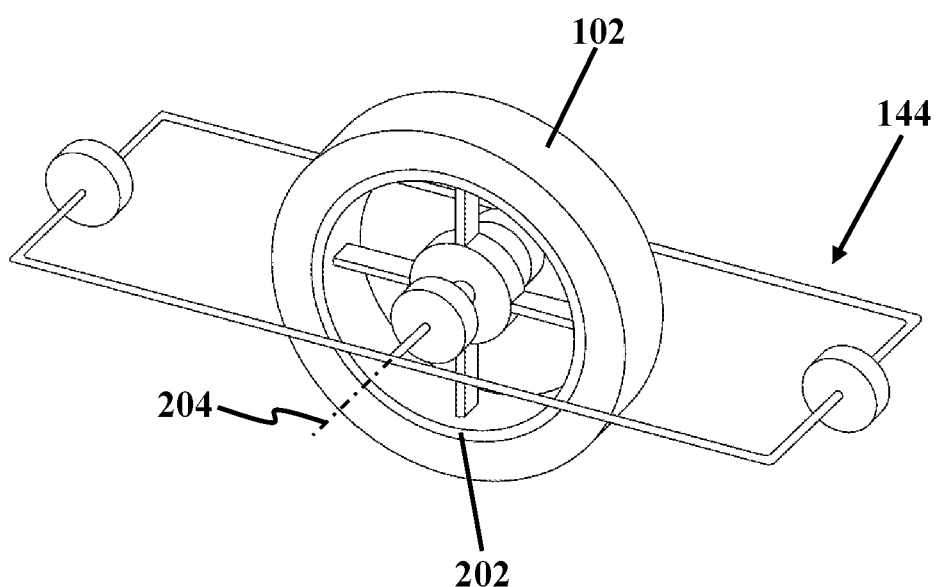
FIG. 2C illustrates a perspective view of an oscillation mechanism coupled with a wheel, consistent with one or more exemplary embodiments of the present disclosure.

FIG. 2C illustrates a perspective view of oscillation mechanism 144 coupled with a wheel 202, consistent with one or more exemplary embodiments of the present disclosure. In an exemplary embodiment, instead of rolling member 142 of FIGS. 2A and 2C, wheel 202 may be coupled with oscillation mechanism 144 and substrate 102 may be a tire mounted on a rim of wheel 202. In an exemplary embodiment, two parallel arms 1440a-b of oscillation mechanism 144 may be attached at their respective midpoints 1441a-b to either sides of wheel 202 on a pivot axis overlapping longitudinal axis 204 of wheel 202. Rolling member 142 may have any other shapes that allow for providing a consistent rolling or rocking motion in system 100.

Referring back to FIGS. 1A and 1B, in an exemplary embodiment, testing apparatus 104 may further include a weight release mechanism 1410 that may be placed at either one of the sides of oscillation mechanism 144 and may be configured to hold and then selectively release one of adjustable weights 1448a or 1448b. In an exemplary embodiment, weight release mechanism 1410 may be mounted on a main chassis 1412 of testing apparatus 104. Main chassis 1412 may include a base support 1414 and a mounting rig 1416 attached on base support 1414.

In an exemplary embodiment, mounting rig 1416 may allow for vertical and horizontal adjustment of the position of weight release mechanism 1410 relative to transparent support member 140. In an exemplary embodiment, mounting rig 1416 may include two parallel vertical poles 1418a-b and a horizontal pole 1421 which may be mounted on two parallel vertical poles 1418a-b by two lock-screw joints 1423a-b at either ends of horizontal pole 1421. In exemplary embodiments, mounting horizontal pole 1421 on two parallel vertical poles 1418a-b by two lock-screw joints 1423a-b may allow for vertically adjusting the height at which horizontal pole 1421 may be mounted relative to transparent support member 140.

Figure 3:
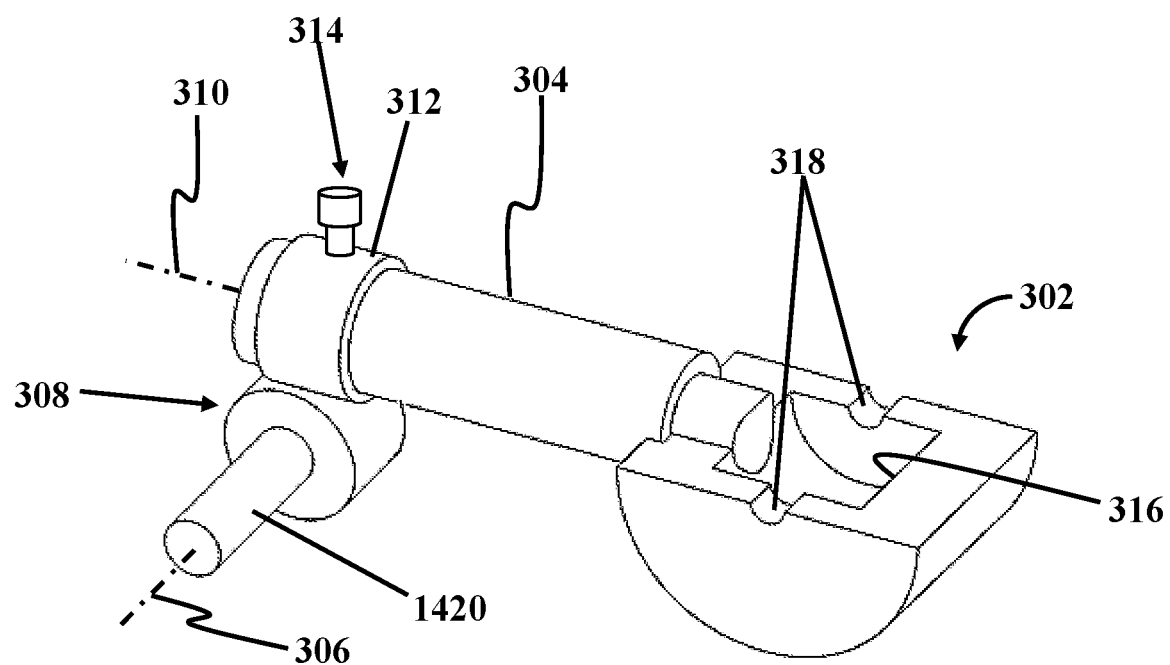
FIG. 3 illustrates a perspective view of a weight release mechanism, consistent with one or more exemplary embodiments of the present disclosure.

FIG. 3 illustrates a perspective view of weight release mechanism 1410, consistent with one or more exemplary embodiments of the present disclosure. Referring to FIGS. 1B and 3, in an exemplary embodiment, weight release mechanism 1410 may include a receptacle 302 mounted at a distal end of a shaft 304. In an exemplary embodiment, receptacle 302 may be a holder that may be sized and shaped to hold either one of adjustable weights 1448a or 1448b. In an exemplary embodiment, receptacle 302 may be an electromagnet that may selectively engage the adjustable weight which is received inside receptacle 302. In detail, holding either one of adjustable weights 1448a or 1448b may entail placing either one of adjustable weights 1448a or 1448b within receptacle 302 and then keeping either one of adjustable weights 1448a or 1448b in place by techniques such as magnetically engaging either one of adjustable weights 1448a or 1448b.

Referring to FIGS. 1A and 3, in an exemplary embodiment, weight release mechanism 1410 may be coupled with control unit 106 and may receive control signals in the form of an electric current from control unit 106. Upon receiving the electric current, a magnetic field may be created in receptacle 302 and either one of adjustable weights 1448a or 1448b, for example, adjustable weight 1448b as shown in FIG. 1A may be held within receptacle 302 under the created magnetic force. When the electric current is cut off by control unit 106, the magnetic field may disappear and receptacle 302 may disengage adjustable weight 1448b and oscillation mechanism 144 may be free to start its rocking motion.

In an exemplary embodiment, weight release mechanism 1410 may be mounted on horizontal pole 1421 by a pivot joint 308 that may allow for pivoting shaft 304 about axis 306 which is parallel to longitudinal axis 1422 and extending/retracting shaft 302 along linear axis 310. In an exemplary embodiment, pivot joint 308 may be coupled with shaft 304 via a ring connection 312 with a lock screw 314 that may be utilized to selectively grip/release shaft 304 from ring connection 312. In an exemplary embodiment, pivot joint 308 may be slidably mounted on horizontal pole 1421 and may allow for horizontally moving weight release mechanism 1410 along horizontal pole 1421. In exemplary embodiments, such a configuration of pivot joint 308 on horizontal pole 1421 may allow for horizontally adjusting the position of weight release mechanism 1410 relative to transparent support member 140.

In an exemplary embodiment, receptacle 302 may be a longitudinal section of a cylinder with a semi-cylindrical recess 316 longitudinally formed on receptacle 302. Semi-cylindrical recess 316 may be sized and shaped to match the shape of and hold either one of adjustable weights 1448a or 1448b. For example, semi-cylindrical recess 316 may be sized and shaped to hold adjustable weight 1448b. In detail, when adjustable weight 1448b is held by receptacle 302 it means that adjustable weight 1448b may sit within semi-cylindrical recess 316. Receptacle 302 may further include two openings 318 at either ends of receptacle 302 to accommodate link 1442b.

In an exemplary embodiment, image capturing device 148 may be a camera mounted below transparent support member 140. Image capturing device 148 may be enclosed by a cover 150 that may extend downward from immediately below lower surface 1406 of transparent support member 140 to immediately above the upper surface of base support 1414. In exemplary embodiments, such configuration of cover 150 may allow for isolating image capturing device 148 from ambient light or any light sources other than light sources 146a-b. In exemplary embodiments, such a configurations may allow for image capturing device 148 to capture high quality consecutive images of rubber footprint of substrate 102 on transparent support member 140 as rolling member rocks substrate 102 back and forth over transparent support member 140, an oscillatory motion urged by oscillation mechanism 144.

Referring to FIG. 1A, in an exemplary embodiment, control unit 106 may be coupled to testing apparatus 104 and user interface unit 108 through wired links, wireless links, or a combination of wired and wireless links. In an exemplary embodiment, control unit 106 may be configured to process the captured images from substrate 102 by image capturing device 148 to observe contact patch and measure rolling resistance of substrate 102. In an exemplary embodiment, control unit 106 may further be configured to control testing apparatus 104 for purposes that may include adjusting the intervals between consecutive images captured by image capturing device 148, adjusting the initial position of weight release mechanism 1410, and adjusting the intensity of light that may be emitted by light sources 146a-b on substrate 102.

In an exemplary embodiment, control unit 106 may include a memory 1062 and a processor 1064. Memory 1062 may include executable instructions that, when executed, cause processor 1064 to perform operations that in an exemplary embodiment may include processing the received images from image capturing device 148 to evaluate contact patch of substrate 102 and to measure rolling resistance of substrate 102. In an exemplary embodiment, such operations may include measuring rolling resistance of substrate 102 based at least in part on damping characteristics of the oscillatory rocking motion of rolling member 142. In exemplary embodiments, such measurements may be performed by operations that may compare consecutively captured images of substrate 102 during oscillatory rocking motion of rolling member 142 on transparent support member 140.

In an exemplary embodiment, user interface unit 108 may be configured to display measurement results of contact patch and rolling resistance of substrate 102. In an exemplary embodiment, user interface unit 108 may include a graphical user interface unit (GUI) that may be optionally configured to receive data input from a user. In an exemplary embodiment, data input by the user may include a desirable interval for capturing the consecutive images by the image capturing device 148, a desirable intensity for light emitted by light sources 146a-b on substrate 102, a desirable value for the initial position of weight release mechanism 1410 or commands regarding the release of adjustable weight 1448b by weight release mechanism 1410.

Figure 4:
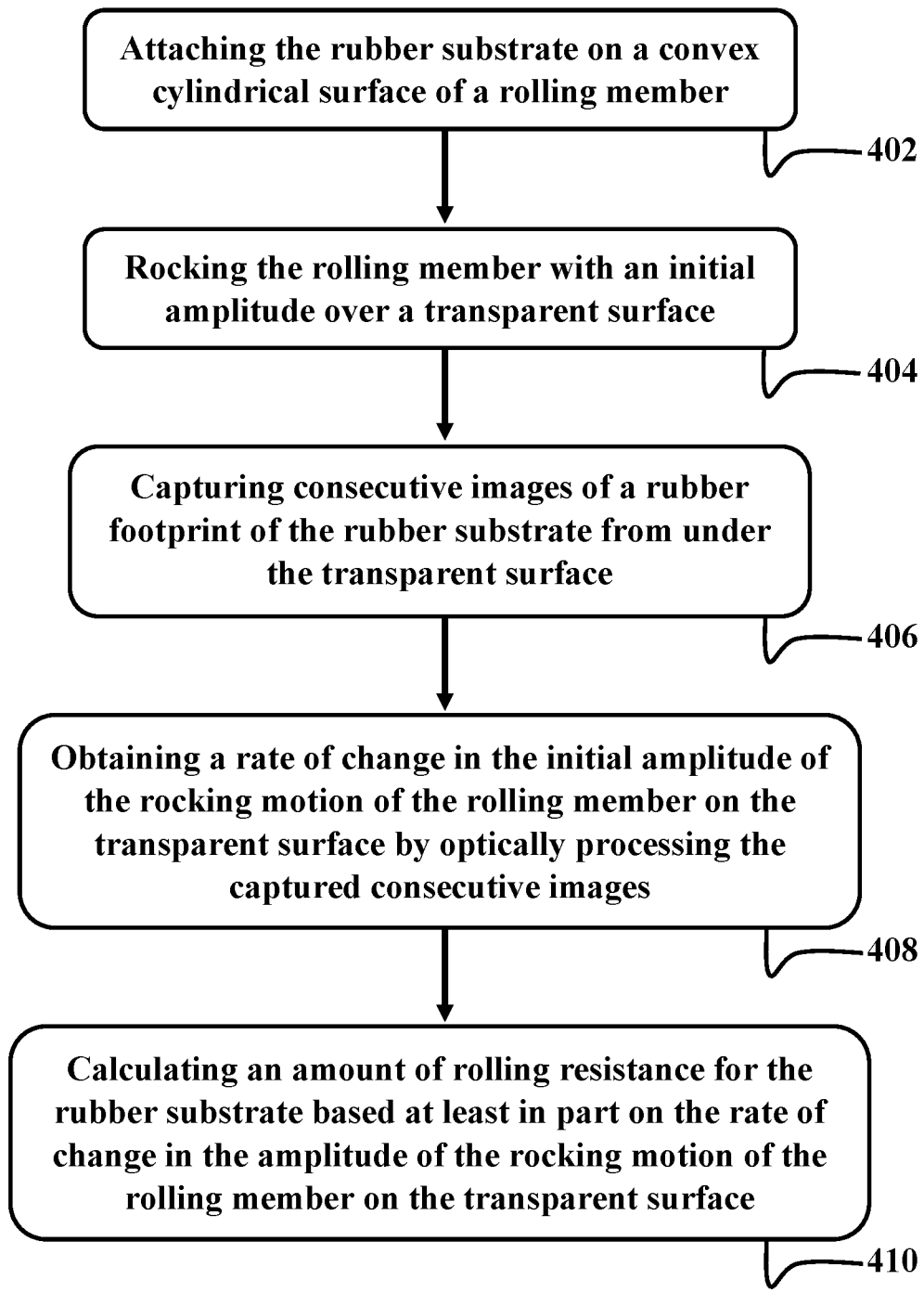
FIG. 4 illustrates a method for testing properties of a rubber substrate, consistent with one or more exemplary embodiments of the present disclosure.

FIG. 4 illustrates a method 400 for testing properties of a rubber substrate, consistent with one or more exemplary embodiments of the present disclosure. In an exemplary embodiment, system 100 of FIG. 1A may be utilized for implementing method 400. Referring to FIG. 4, method 400 may include a step 402 of attaching the rubber substrate on a convex cylindrical surface of a rolling member, a step 404 of rocking the rolling member with an initial amplitude over a transparent surface, a step 406 of capturing consecutive images of a rubber footprint of the rubber substrate from under the transparent surface, a step 408 of obtaining a rate of change in the initial amplitude of the rocking motion of the rolling member on the transparent surface by optically processing the captured consecutive images, and a step 410 of calculating an amount of rolling resistance for the rubber substrate based at least in part on the rate of change in the amplitude of the rocking motion of the rolling member on the transparent surface.

Referring to FIGS. 1A and 4, in an exemplary embodiment, step 402 may involve attaching the rubber substrate on a convex cylindrical surface of a rolling member, for example, rubber substrate may be a rubber sheet such as substrate 102 that may be attached on convex cylindrical surface 1420 of rolling member 142.

In an exemplary embodiment, step 404 of rocking the rolling member with an initial amplitude over a transparent surface may include rocking the rolling member with an initial amplitude over the transparent surface utilizing an oscillation mechanism. For example, rolling member 142 may be rocked over transparent support member 140 utilizing oscillation mechanism 144. In an exemplary embodiment, rocking the rolling member with the initial amplitude over the transparent surface may include adjusting the initial amplitude of the rocking motion of the rolling member, for example, placing adjustable weight 1448b of oscillation mechanism 144 within weight release mechanism 1410 may put oscillation mechanism 144 in an initial orientation which in turn may determine an initial position and orientation of rolling member 142 over transparent support member 140. With further reference to FIGS. 1B and 3, the position of weight release mechanism 1410 may be changed relative to transparent support member 140 by changing the height of weight release mechanism 1410 by vertically moving horizontal pole 1421 on vertical poles 1418a-b, changing the horizontal position of weight release mechanism 1410 by sliding weight release mechanism 1410 on horizontal pole 1421 along an axis parallel to longitudinal axis 1422, changing the lateral distance of weight release mechanism 1410 with transparent support member 140 by extending/retracting shaft 302 along linear axis 310. In an exemplary embodiment, initial position of weight release mechanism 1410 may be manipulated in order to adjust the initial position and orientation of oscillation mechanism 144 which in turn may determine the initial position and orientation of rolling member 142 before rolling member 142 may start its rocking motion. This initial position and orientation of rolling member 142 may set the initial amplitude at which oscillation mechanism 144 may urge rolling member 142 to rock back and forth on transparent support member 140. As used herein, a rocking motion may refer to a motion similar to the motion of a seesaw in oscillation mechanism 144 about longitudinal axis 1422 that may urge rolling member 142 to rock back and forth about longitudinal axis 1422.

Referring to FIGS. 1A and 4, in an exemplary embodiment, step 406 may involve capturing consecutive images of a rubber footprint of the rubber substrate from under the transparent surface. For example, image capturing device 148 may be utilized for capturing consecutive images of the rubber footprint of substrate 102 from below transparent support member 140 and light sources 146a-b may be utilized to shine light on the rubber footprint of substrate 102 to allow for high quality images to be captured of the rubber footprint of substrate 102. As used herein, capturing consecutive images may also refer to continuously filming the back and forth motion of the rubber footprint on transparent support member 140.

Figure 5A:
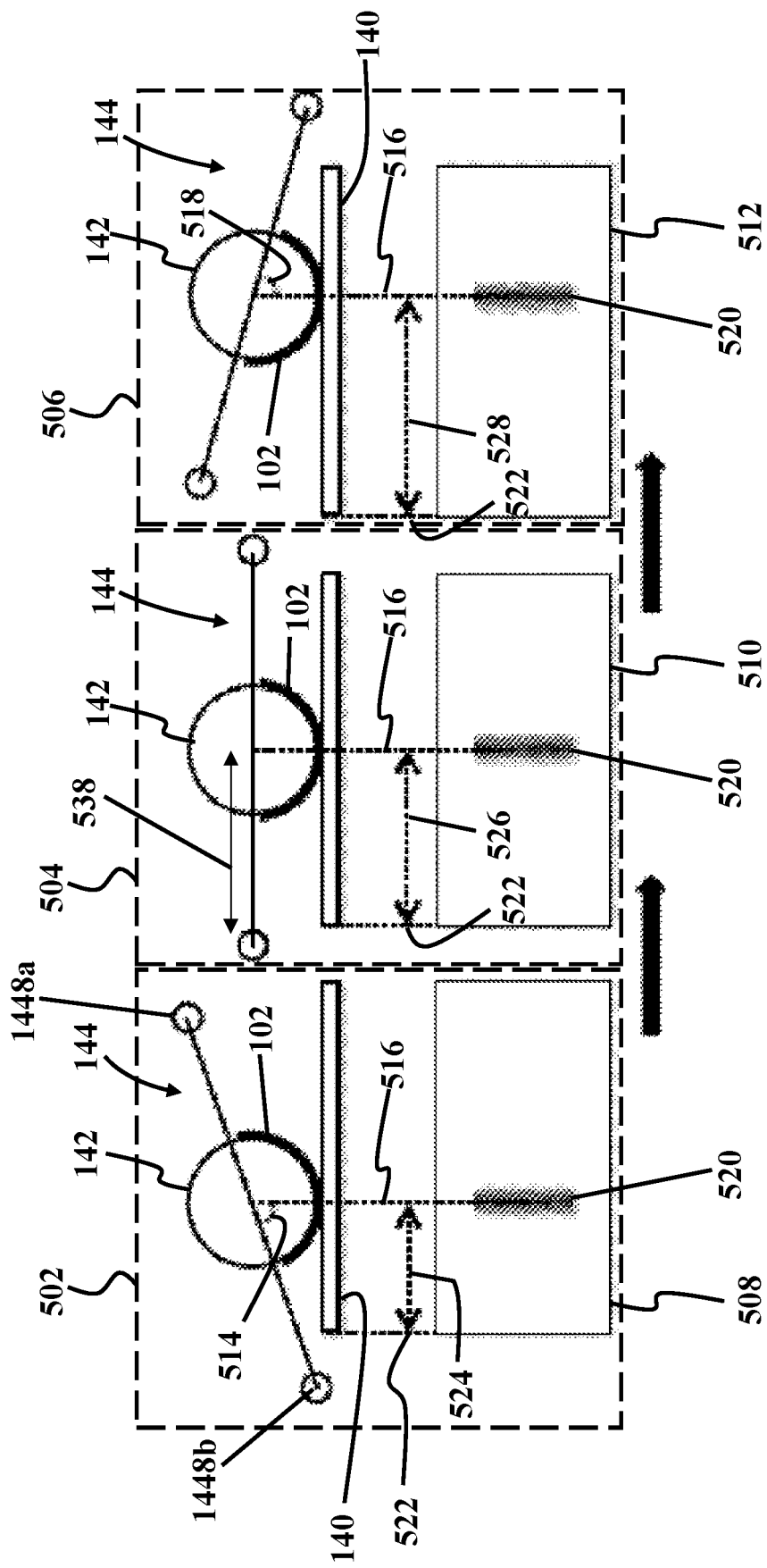
FIG. 5A illustrates a schematic of a rolling member and an oscillation mechanism in three stages during rocking motion of the rolling member and corresponding images captured by an image capturing device, consistent with one or more exemplary embodiments of the present disclosure.

FIG. 5A illustrates a schematic of rolling member 142 and oscillation mechanism 144 in three stages 502, 504, and 506 during rocking motion of rolling member 142 and corresponding images 508, 510, and 512 captured by image capturing device 148, consistent with one or more exemplary embodiments of the present disclosure. In an exemplary embodiment, as rolling member 142 rolls forward on transparent support member 140, a corresponding rubber foot print 520 of substrate 102 captured in corresponding images 508, 510, and 512 also moves forward. Therefore, the back and forth rocking motion of rolling member 142 on transparent support member 140 may be tracked in corresponding images 508, 510, and 512 as the back and forth motion of rubber foot print 520.

Referring to FIGS. 1A and 4, in an exemplary embodiment, step 408 of obtaining the rate of change in the initial amplitude of the rocking motion of the rolling member on the transparent surface by optically processing the captured consecutive images may include tracking a back and forth movement of the rubber footprint of the rubber substrate on the transparent surface by processing the captured consecutive images by an image processor. For example, the consecutive images that may be captured by image capturing device 148 may be transferred to control unit 106 where the captured images may be stored on memory 1062. The stored captured images may then be read from memory 1062 by processor 1064 during the test or at some time after the test has been run. Processor 1064 may optically process the captured images to track the back and forth movement of the rubber footprint of substrate 102 based at least in part on the position of the rubber footprint on transparent support member 140 at every instance of the test. In an exemplary embodiment, the test may begin by releasing oscillation mechanism 144 from its initial orientation by weight release mechanism 1410 and the test may end with an amplitude of the rocking motion of oscillation mechanism 144 reaching zero. In other words, the test ends when the back and forth rocking motion of oscillation mechanism 144 comes to an end.

Figure 5B:
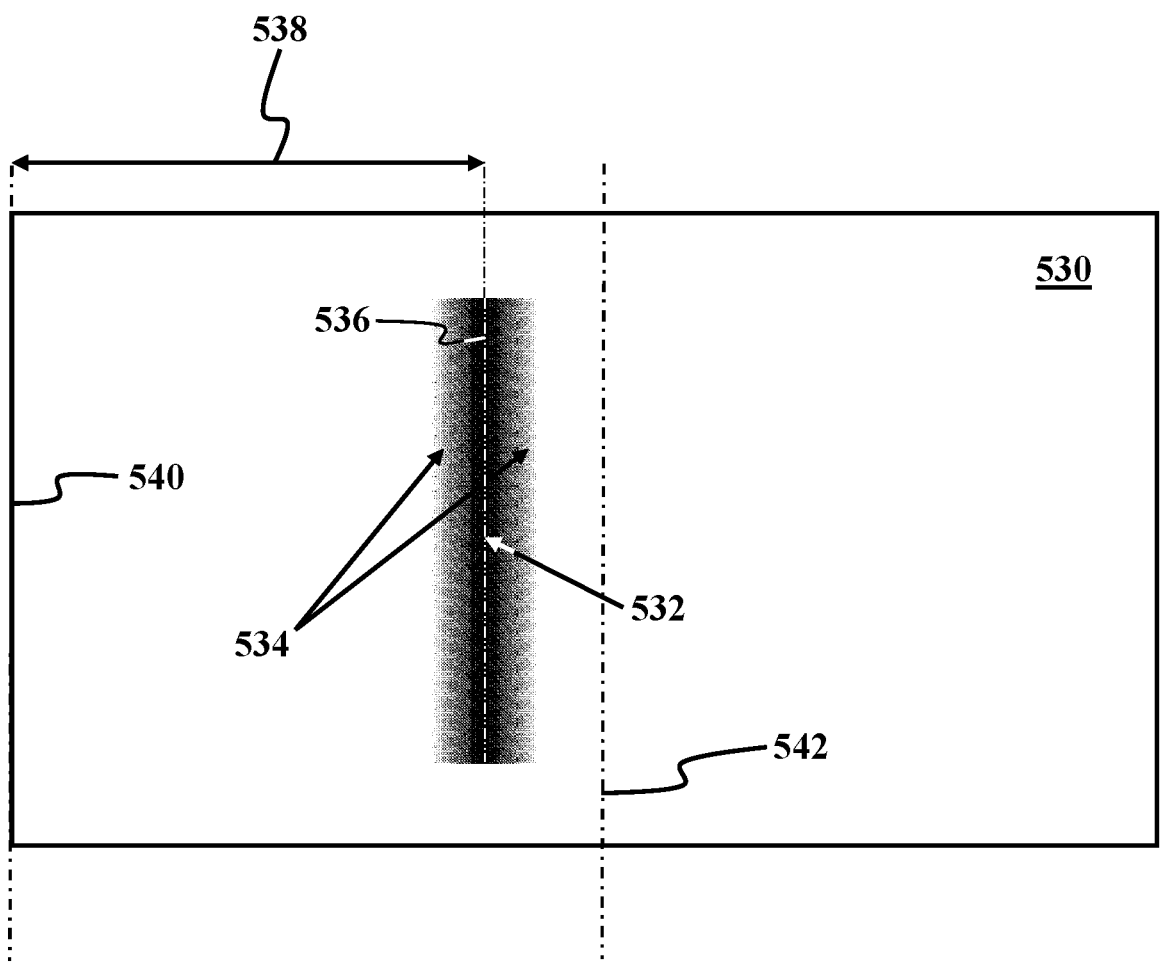
FIG. 5B illustrates a schematic of an exemplary image of a rubber footprint of a rubber substrate captured by an image capturing device, consistent with one or more exemplary embodiments of the present disclosure.

FIG. 5B illustrates a schematic of an exemplary image 530 of rubber footprint of a rubber substrate captured by image capturing device 148, consistent with one or more exemplary embodiments of the present disclosure. Pixel density within the captured rubber footprint is higher near its central region 532 where the pressure exerted on the rubber substrate is higher and pixel density is lower toward the edges 534 of rubber footprint, where the pressure exerted on the rubber substrate is lower. With further reference to FIGS. 1A and 4, in an exemplary embodiment, step 408 of obtaining the rate of change in the initial amplitude of the rocking motion of the rolling member on the transparent surface may include processing the captured images to find a pressure center 536 for the rubber footprint by finding a region with the highest pixel density and then calculating, at any given moment during the test, a distance 538 between pressure center 536 and a reference line which may be one of the lateral edges of the captured image, for example edge 540. This way, in exemplary embodiments, a range of motion may be obtained for the rubber footprint which may be considered as a measure of how far rolling member 142 is rocking back and forth. In an exemplary embodiment, the position of rubber footprint at any given moment during the test may be calculated as a distance between pressure center 536 and a center line 542. In an exemplary embodiment, center line 542 may be the midpoint of the motion path of rolling member 142.

Figure 6:
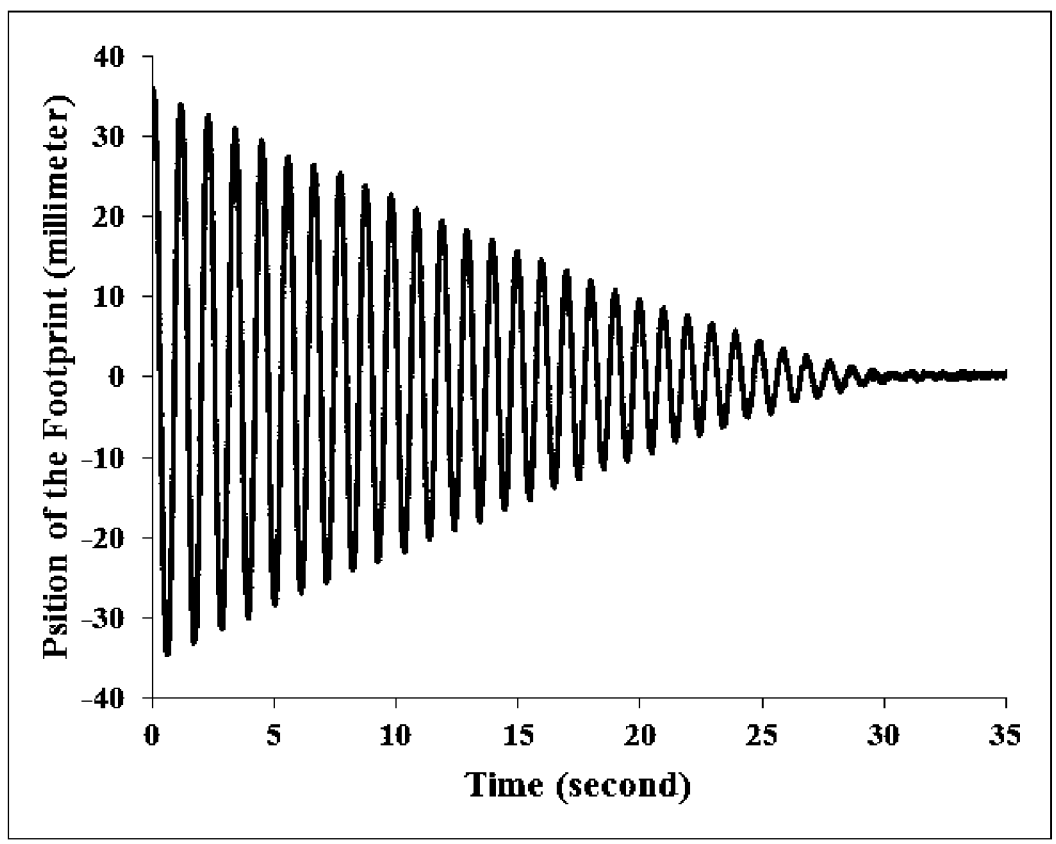
FIG. 6 illustrates a graph of rubber footprint position versus time during an exemplary test, consistent with one or more exemplary embodiments of the present disclosure.

FIG. 6 illustrates a graph of rubber footprint position versus time during an exemplary test, consistent with one or more exemplary embodiments of the present disclosure. With further reference to FIG. 5B, in this exemplary graph, rubber footprint position is calculated as a distance between pressure center 536 of the rubber footprint and center line 542. Referring to FIGS. 5A and 6, it is evident that the range of motion or the amplitude for rolling member 142 decreases with time. The amount of rolling resistance of substrate 102 is proportional to the rate at which the amplitude decreases. For example, for a substrate with a high rolling resistance the amplitude decreases rapidly while for a substrate with a lower rolling resistance the amplitude decreases more slowly. The rate of decrease of amplitude of rocking motion of rolling member 142 may be a measure of the rolling resistance of substrate 102. In the exemplary test shown in FIG. 6, the amplitude has decreased down to zero after 30 seconds, meaning that rolling member 142 starts its rocking motion at a high initial amplitude and then as time goes by, due to the rolling resistance of substrate 102, the initial amplitude starts to decrease an after 30 seconds the amplitude becomes zero and rolling member 142 stops.

Referring to FIGS. 1A and 4, in an exemplary embodiment, step 410 involves calculating an amount of rolling resistance for the rubber substrate based at least in part on the rate of change in the amplitude of the rocking motion of the rolling member on the transparent surface. For example, memory 1062 may further include executable instructions that when executed by processor 1064, may urge control unit 106 to optically process the captured images to find pressure center of the rubber footprint of substrate 102 at any given moment during the test as was discussed in connection with FIG. 5B. Then control unit 106 may utilize the movement of pressure center of substrate 102 to calculate change in the amplitude of the rocking motion of the rolling member 142 on transparent support member 140.

Referring to FIGS. 1A and 5B, in an exemplary embodiment, memory 1062 may further include executable instructions that when executed by processor 1064, may urge control unit 106 to calculate a pressure distribution for the rubber footprint by dividing an average pixel density of captured images by a maximum pixel density of the captured images. For example, in exemplary image 530, a pressure distribution may be calculated by dividing an average pixel density of image 530 by the pixel density of pressure center 536.

Referring to FIG. 5A, in an exemplary embodiment, in stage 502 which may be an exemplary initial stage of a forward movement of rolling member 142, oscillation mechanism 144 may be arranged such that it makes an initial angle 514 of $\theta_0$ with a vertical axis 516. Stage 504 is a stage during a forward movement of rolling member 142, where oscillation mechanism 144 makes a 90° angle with vertical axis 516, and stage 506 is an exemplary final stage of a forward movement of rolling member 142, where oscillation mechanism 144 may make a final angle 518 of $\theta_1$ with vertical axis 516. In an exemplary embodiment, corresponding images 508, 510, and 512 captured by image capturing device 148 show rubber footprint 520 of substrate 102. As rolling member 142 rolls from initial stage 502 to final stage 506, a distance between a pressure center of rubber footprint 520 and a reference line 522 may increase from an initial distance 524 of $a_0$ to a final distance 528 of $a_1$. In stage 504, pressure center of ground rubber footprint 520 is at a distance 526 of $a_\infty$ from reference point 522. With further reference to FIG. 1A, in an exemplary embodiment, control unit 106 may be calibrated to calculate the angle that oscillation mechanism 144 makes with vertical axis 516 at any given moment during the test and the angle may be labeled as $\theta_n$, which is the angle of oscillation mechanism 144 with vertical axis 516 in the $n^{th}$ oscillation of rolling member 142.

In an exemplary embodiment, memory 1062 may further include executable instructions that when executed by processor 1064, may urge control unit 106 to calculate rolling resistance of substrate 102 by Equation (1) below:

$$RR = \sum_{n=0}^{n=\infty} \frac{2mgL[\cos\theta_0]}{R\theta_n} = \frac{2mgL[\cos\theta_0]}{\sum_{n=0}^{n=\infty} R\theta_n} \qquad \text{Equation (1)}$$

In Equation (1) above, RR is the amount of rolling resistance, m is the mass of each of adjustable weights 1448a-b, g is the standard gravity, L is the distance between either one of adjustable weights 1448a or 1448b from the center of rolling member 142, $\theta_0$ is the initial angle of oscillation mechanism 144 with vertical axis 516, $\theta_n$ is the angle of oscillation mechanism 144 with vertical axis 516 in the $n^{th}$ oscillation, and R is the radius of rolling member 142.

Referring back to FIG. 1B, as mentioned in preceding sections, testing apparatus 104 of exemplary embodiments of the present disclosure may utilize oscillation mechanism 144 to rock rolling member 142 back and forth on transparent support member 140. Two adjustable weights 1448a-b of oscillation mechanism 144 may be coupled with rolling member 142 such that adjustable weights 1448a-b may be symmetrically arranged at either sides of oscillation mechanism 144. In exemplary embodiments, symmetrical arrangement of adjustable weights 1448a-b may allow for ensuring a stable rocking motion of rolling member 142 in a straight motion path without any deviation from the motion path as would be the case if a single pendulum were utilized for inducing the rocking motion. Moreover, in exemplary embodiments, utilizing symmetrical arrangement of adjustable weights 1448a-b may allow for ensuring an even load distribution of rolling member 142 on substrate 102. Furthermore, weight release mechanism 1410 may allow for releasing oscillation mechanism 144 in the same manner for each sample substrate tested. This may standardize the motion of rolling member 142 so that consistent initial conditions such as consistent initial amplitudes may be provided to testing apparatus 104 for each test run and for each individual sample. In other words, utilizing weight release mechanism 1410 may allow for providing a same amplitude for rocking motion of rolling member 142 in different test runs. Therefore, exemplary systems consistent with one or more exemplary embodiments of the present disclosure allows for an accurate measurement and calculation of the shape and size of the rubber footprint of substrate 102 on transparent support member 140, the pressure distribution within the rubber footprint of substrate 102, and the amount of the rolling resistance of substrate 102.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A system for testing properties of a substrate, the system comprising:
   a transparent support member comprising a transparent contact surface;
   a rolling member comprising a cylindrical convex surface with the substrate attached on the cylindrical convex surface, the cylindrical convex surface configured to be in constant contact with the transparent contact surface;
   an oscillation mechanism coupled with the rolling member configured to drive an oscillatory rocking motion of the rolling member about a longitudinal axis of the rolling member, the oscillation mechanism comprising:
      two parallel arms attached at their respective midpoints to either base ends of the rolling member on a pivot axis overlapping the longitudinal axis of the rolling member, the two parallel arms attached to one another at respective ends of the two parallel arms by two links; and
      two adjustable weights, each of the two adjustable weights mounted on a respective link of the two links;
   a light source arranged at one side of the transparent body such that light from the light source emitted within the transparent support member; and
   an image capturing device placed below the transparent contact surface configured to capture images of a rubber footprint of the substrate through the transparent support member.

2. The system according to claim 1, further comprising a control unit coupled with the image capturing device, the control unit comprising:
   a processor; and
   a memory configured to store executable instructions to cause the processor to:
      identify a pressure center for the rubber footprint of the substrate based on the images captured by the image capturing device, the pressure center corresponding to a region within the images of the rubber footprint with the highest black pixel density; and
      obtain a rate of change in a motion range of the rubber footprint by tracking back and forth motion of the pressure center of the images.

3. The system according to claim 2, wherein the memory is configured to store further executable instructions to cause the processor to calculate a pressure distribution within the rubber footprint by dividing an average black pixel density of the captured images by the highest black pixel density in the images.

4. The system according to claim 2, wherein the memory is configured to store further executable instructions to cause the processor to calculate rolling resistance of the substrate by equation below:

$$RR = \sum_{n=0}^{n=\infty} \frac{2mgL[\cos\theta_0]}{R\theta_n} = \frac{2mgL[\cos\theta_0]}{\sum_{n=0}^{n=\infty} R\theta_n}$$

where, RR is the amount of rolling resistance, m is the mass of each of the two adjustable weights, g is the standard gravity, L is the distance between either one of the two adjustable weights from a center of rolling member, $\theta_0$ is the initial angle of oscillation mechanism with a normal axis of the transparent support member, $\theta_n$ is the angle of oscillation mechanism with the normal axis of the transparent support member in an $n^{th}$ oscillation of the rocking motion of the rolling member, and R is a radius of the rolling member.

5. The system according to claim 1, wherein the longitudinal axis of the rolling member is an axis passing through a center of the mass of the rolling member on a similar plane with a rolling direction of the rolling member perpendicular to the rolling direction.

6. The system according to claim 1, wherein the rolling member further comprising two adjustable side-weights removably attached to either base end of the rolling member.

7. The system according to claim 1, further comprising a main chassis, the main chassis comprising:
   a base support; and
   a mounting rig attached on the base support, the mounting rig comprising:
      two parallel vertical poles mounted on the base support; and
      a horizontal pole mounted between the two parallel vertical poles with an adjustable height relative to the transparent support member.

8. The system according to claim 7, further comprising a weight release mechanism mounted on the horizontal pole, the weight release mechanism comprising:
   a shaft pivotally mounted on the horizontal pole at a first end of the shaft; and
   a receptacle attached to a second end of the shaft, the receptacle comprising an electromagnet selectively engaging one of the two adjustable weights.

9. The system according to claim 8, wherein the receptacle is a longitudinal section of a cylinder including a semi-cylindrical recess longitudinally formed on the receptacle, the semi-cylindrical recess configured to hold one of the two adjustable weights.

10. The system according to claim 1, wherein the rolling member is a cylinder-shaped roller with two adjustable side weights removably attached to either base ends of the cylinder-shaped roller.

11. The system according to claim 1, wherein the rolling member is a longitudinal section of a cylinder including a lower cylindrical convex surface and an upper flat surface, the substrate attached under the lower cylindrical convex surface.

12. The system according to claim 11, wherein the rolling member further comprises adjustable weights removably mounted on the upper flat surface.

13. The system according to claim 1, wherein the rolling member is a wheel with the substrate attached to a rim of the wheel.

14. The system according to claim 1, wherein the transparent support member is a box-shaped member with parallel and flat upper surface and lower surface, the upper surface providing the transparent contact surface.

15. A method for testing properties of a rubber substrate, the method comprising:
    attaching the rubber substrate on a convex cylindrical surface of a rolling member;
    rocking the rolling member with an initial amplitude over a transparent surface;
    capturing consecutive images of a rubber footprint of the rubber substrate from under the transparent surface;
    obtaining, using one or more processors, a rate of change in the initial amplitude of the rocking motion of the rolling member on the transparent surface based at least in part on a rate of change in a range of back and forth motion of the rubber footprint by optically processing the captured consecutive images; and
    calculating, using the one or more processors, an amount of rolling resistance for the rubber substrate based at least in part on the rate of change in the amplitude of the rocking motion of the rolling member on the transparent surface.

16. The method according to claim 15, wherein rocking the rolling member with the initial amplitude over the transparent surface comprises:
    coupling the rolling member with an oscillation mechanism, the oscillation mechanism comprising:
        two parallel arms attached at their respective midpoints to either base ends of the rolling member on a pivot axis overlapping a longitudinal axis of the rolling member, the two parallel arms attached to one another at respective ends of the two parallel arms by two links; and
        two adjustable weights, each of the two adjustable weights mounted on a respective link of the two links;
    adjusting the initial amplitude by adjusting an initial orientation of the two parallel arms with respect to the transparent surface; and
    releasing the oscillation mechanism from the initial orientation to freely oscillate in a rocking motion back and forth about the longitudinal axis of the rolling member.

17. The method according to claim 16, wherein the longitudinal axis of the rolling member is an axis passing through a center of the mass of the rolling member on a similar plane with a rolling direction of the rolling member perpendicular to the rolling direction.

18. The method according to claim 15, wherein obtaining the rate of change in the initial amplitude of the rocking motion of the rolling member on the transparent surface includes optically processing the captured images to track the position of the rubber footprint on the transparent surface at every instance of the test, the test beginning with releasing the oscillation mechanism from the initial orientation and ending with the rocking motion of the oscillation mechanism coming to an end.

19. The method according to claim 15, wherein obtaining the rate of change in the initial amplitude of the rocking motion of the rolling member on the transparent surface comprises:
    processing the captured images to find a pressure center for the rubber footprint by finding a region with the highest black pixel density; and
    calculating, at any given moment a distance between the pressure center and a reference line.

20. The method according to claim 19, wherein the reference line is either one of edges of the captured images, the reference line perpendicular to a direction of a motion of the pressure center.

* * * * *